(12) United States Patent
Wollenweber et al.

(10) Patent No.: US 8,699,771 B2
(45) Date of Patent: Apr. 15, 2014

(54) METHOD AND APPARATUS FOR REDUCING MOTION-RELATED IMAGING ARTIFACTS

(75) Inventors: Scott David Wollenweber, Waukesha, WI (US); Alexander Ganin, Whitefish Bay, WI (US); Kris Filip Johan Jules Thielemans, Putney (GB); Larry Pierce, Seattle, WA (US); Adam Alessio, Seattle, WA (US); Paul Kinahan, Seattle, WA (US); Chi Liu, Seattle, WA (US)

(73) Assignee: General Electric Company, Schenectady, NY (US)

( * ) Notice: Subject to any disclaimer, the term of this patent is extended or adjusted under 35 U.S.C. 154(b) by 1146 days.

(21) Appl. No.: 12/622,006

(22) Filed: Nov. 19, 2009

(65) Prior Publication Data

US 2011/0116695 A1 May 19, 2011

(51) Int. Cl.
*A61B 6/03* (2006.01)

(52) U.S. Cl.
USPC .............................................. 382/131; 378/8

(58) Field of Classification Search
USPC .............................................. 382/131; 378/8
See application file for complete search history.

(56) References Cited

U.S. PATENT DOCUMENTS

| 4,994,965 | A | 2/1991 | Crawford et al. |
| 5,057,682 | A | 10/1991 | Michon et al. |
| 6,198,959 | B1 | 3/2001 | Wang |
| 2003/0009098 | A1* | 1/2003 | Jack et al. ............... 600/410 |
| 2005/0113674 | A1 | 5/2005 | Salla et al. |
| 2007/0081704 | A1* | 4/2007 | Pan et al. ............... 382/128 |
| 2007/0232903 | A1* | 10/2007 | Hamill .................. 600/426 |
| 2013/0085375 | A1* | 4/2013 | Hamill et al. .......... 600/413 |

OTHER PUBLICATIONS

Liu et al., Quiescent phase respiratory gating for PET/CT, May 2009, The Journal of Nuclear Medicine Meeting Abstracts, vol. 50, Abstract No. 1473.*
Sonke et al., Variability of Four-Dimensional Computed Tomography Patient Models, Feb. 2008, International Journal of Radiation Oncology in Physics and Biology, vol. 70, No. 2, pp. 590-598.*
Guckenberger et al., Influence of retrospective sorting on image quality in respiratory correlated computed tomography, 2007, Radiotherapy and Oncology, vol. 85, pp. 223-231.*
Van Elmpt et al., Optimal gating compared to 3D and 4D PET reconstruction for characterization of lung tumors, 2011, European Journal of Nuclear Molecular Imaging, vol. 38, pp. 843-855.*
Kawano T, Ohtake E, Inoue T. Deep-inspiration breath-hold PET/CT of lung cancer: maximum standardized uptake value analysis of 108 patients. J Nucl Med. 2008;49:1223-1231.

(Continued)

*Primary Examiner* — Toan Ton
*Assistant Examiner* — John Corbett
(74) *Attorney, Agent, or Firm* — The Small Patent Law Group; Dean D. Small

(57) ABSTRACT

A method and apparatus are provided for reducing motion related imaging artifacts. The method includes obtaining an image data set of a region of interest in an object, obtaining a motion signal indicative of motion of the region of interest, determining at least one quiescent period of at least a portion of the motion signal, extracting image data from the image data set that is within the determined quiescent period to form an image data subset, and generating an image of the region of interest using the image data subset.

19 Claims, 15 Drawing Sheets

(56) References Cited

OTHER PUBLICATIONS

Allen-Auerbach M, Yeom K, Park J, et al. Standard PET/CT of the chest during shallow breathing is inadequate for comprehensive staging of lung cancer. J Nucl Med. 2006;47:298-301.

Cohade C, Osman M, Marshall LN, et al. PET-CT: accuracy of PET and CT spatial registration of lung lesions. *Eur J Nucl Med Mol Imaging*. 2003;30:721-726.

Erdi YE, Nehmeh SA, Pan T, et al. The CT motion quantitation of lung lesions and its impact on PET-measured SUVs. J Nucl Med. 2004;45:1287-1292.

Goerres GW, Burger C, Kernel E, et al. Respiration-induced attenuation artifact at PET/CT: technical considerations. Radiology. 2003;226:906-910.

Nehmeh SA, Erdi YE, Meirelles GSP, Squire O, Larson SM, Humm JL, Schoder H. Deep-inspiration breath-hold PET/CT of the thorax. *J Nucl Med*. 2007;48:22-26.

Meirelles GSP, Erdi YE, Nehmeh SA, Squire OD, Larson SM, Humm JL, Schoder H. Deep-inspiration breath-hold PET/CT: Clinical findings with a new technique for detection and characterization of thoracic lesions. *J Nucl Med*. 2007;48:712-719.

Osman MM, Cohade C, Nakamoto Y, et al. Clinically significant inaccurate localization of lesions with PET/CT: frequency in 300 patients. *J Nucl Med*. 2003;44:240-243.

Osman MM, Cohade C, Nakamoto Y, et al. Respiratory motion artifacts on PET emission images obtained using CT attenuation correction on PET-CT. *Eur J Nucl Med Mol Imaging*. 2003;30:603-606.

Pan TS, Mawlawi C, Nehmeh SA, et al. Attenuation correction of PET images with respiration-averaged CT images in PET/CT. *J Nucl Med*. 2005;46:1481-1487.

Wink N, Panknin C, Solberg TD. Phase versus amplitude sorting of 4D-CT data. *J Appl Clin Med Phys*. 2006;7:77-85.

Search Report, General Electric Company, Date: Oct. 24, 2009, Searcher: Nagaraja, KA, e-mail: wkcservices.jfwtc@ge.com, (6) pgs.

Chi Liu, et al., Impact of respiratory motion on tumor quantification and delineation in wholebody PET/CT, J Nucl Med. 2009, 50 (Supplement 2): 233, http://jnumedmtg.snmjournals.org/cgi/content/meeting_abstract/50/2_MeetingAbstracts/233, (2) pgs.

\* cited by examiner

METHOD AND APPARATUS FOR REDUCING MOTION-RELATED IMAGING ARTIFACTS

BACKGROUND OF THE INVENTION

The subject matter disclosed herein relates generally to imaging systems, and more particularly, embodiments relate to an apparatus and method for reducing image artifacts that are produced by movement of an object.

Multi-modality imaging systems exist that scan using different modalities, for example, Computed Tomography (CT), Magnetic Resonance Imaging (MRI), Positron Emission Tomography (PET), and Single Photon Emission Computed Tomography (SPECT). During operation, conventional imaging systems may exhibit image quality that is affected by motion of the object being imaged. For example, PET/CT imaging of the lung and abdomen region is generally affected by patient respiratory motion. The respiratory motion may cause an underestimation of tumor uptake and an overestimation of tumor volume.

Conventional imaging systems may utilize several methods to account for respiratory motion related artifacts. These methods include respiratory gated 4D PET/CT, deep-inspiration-breath-hold (DIBH) PET/CT, post-processing image registration methods and motion-corrected PET reconstruction. While the above methods have achieved improvements in motion correction, these methods also have certain limitations. For example, in respiratory gating, although each gated image is less affected by respiratory motion, the total detected counts are divided into several bins. Thus each gated image is much noisier than the non-gated ones. However, for patients with irregular breathing patterns with respiratory amplitude variability, the gating methods, particularly the phase gating methods, may result in unsatisfactory image quality. The DIBH PET/CT method provides a theoretically motionless image and better CT-PET match for the deep inspiration phase, however, the total acquisition time is significantly longer than that of the conventional PET/CT study if a similar amount of detected accounts are required. Image registration methods transform each gated image and sum the transformed images at the end. However, these methods significantly depend on the accuracy of the motion estimation technique used, like the widely used optical flow method, which has strict assumptions, such as intensity constraints, that are not strictly valid in PET/CT gated images.

Moreover, motion vectors may be estimated from either 4D PET or 4D CT images. However, the 4D PET images are relatively noisy and may yield an unreliable estimation. The 4D CT images are relatively low noise, but the 4D CT images are acquired during different breathing cycles from those of the 4D PET images. Thus, the motion information estimated using 4D CT images may not match that of the 4D PET images, resulting in motion estimation errors.

BRIEF DESCRIPTION OF THE INVENTION

In one embodiment, a method for reducing motion related imaging artifacts is provided. The method includes obtaining an image data set of a region of interest in an object, obtaining a motion signal indicative of motion of the region of interest, determining at least one quiescent period of at least a portion of the motion signal, extracting image data from the image data set that is within the determined quiescent period to form an image data subset, and generating an image of the region of interest using the image data subset.

In another embodiment, a multi-modality imaging system is provided. The multi-modality imaging system includes a first modality unit, a second modality unit, and a quiescent period gating module operationally coupled to the first and second modality units. The quiescent period gating module is programmed to receive a motion signal indicative of motion of the region of interest, determine at least one quiescent period of at least a portion of the motion signal, extract data from the data set that is within the determined quiescent period to form an image data subset, and generate an image of the region of interest using the data subset.

In a further embodiment, a computer readable medium encoded with a program is provided. The program is programmed to instruct a computer to obtain an image data set of a region of interest in an object from at least one of a PET imaging system and a CT imaging system, obtain a motion signal indicative of motion of the region of interest, determine at least one quiescent period of at least a portion of the motion signal, extract image data from the image data set that is within the determined quiescent period to form an image data subset, and generate an image of the region of interest using the image data subset.

DETAILED DESCRIPTION OF THE INVENTION

Figure 1:
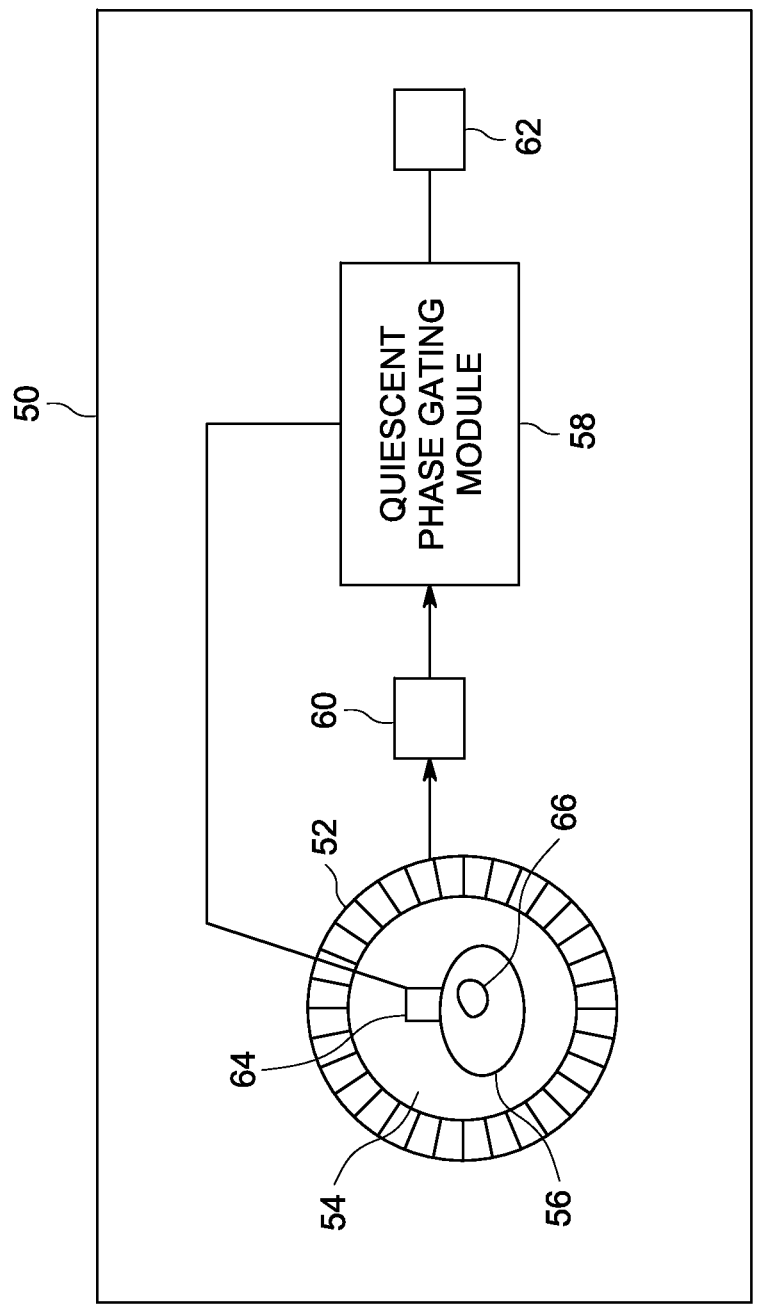
FIG. 1 is a pictorial view of an exemplary multi-modality imaging system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

FIG. 1 is a schematic block diagram of an exemplary imaging system 50 in accordance with an embodiment of the present invention. The imaging system 50 includes a detector 52 having a central opening 54 therethrough. The opening 54 is configured to receive an object or patient, such as object 56 therein. The imaging system 50 also includes a quiescent period gating module 58. Quiescent as used herein refers to a respiratory state of relative inactivity, repose, and/or tranquility. During operation, the output from the detector 52, referred to herein as an image data set 60 or raw image data, is transmitted to the quiescent period gating module 58. The quiescent period gating module 58 is configured to utilize the image data set 60 to identify and remove motion related imaging artifacts from the image data set 60 to form an image data subset 62. The image data subset 62 is then used to generate an image of the object 56.

Figure 2A:
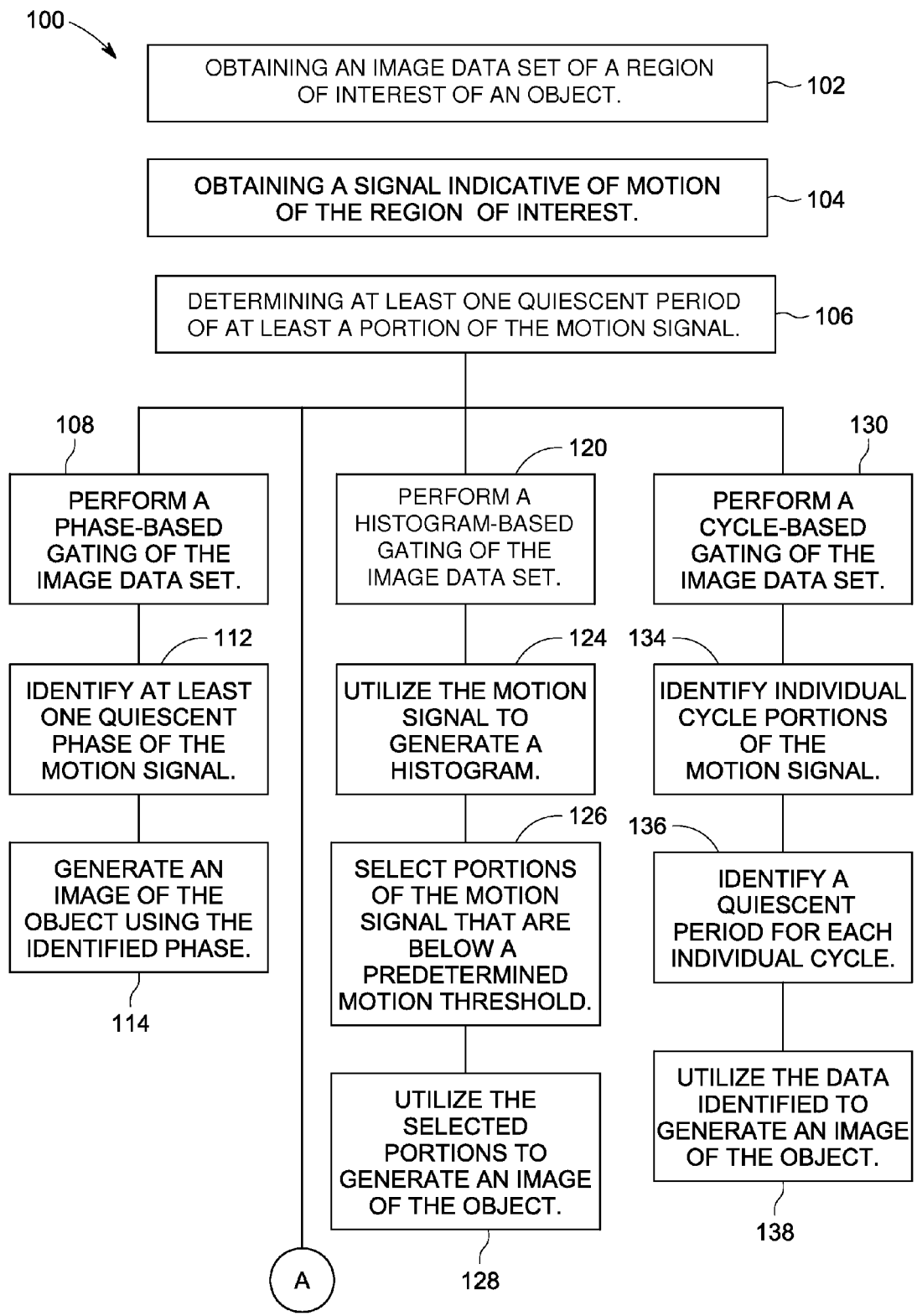
FIGS. 2A and 2B are a flowchart illustrating an exemplary method in accordance with various embodiments for reducing motion artifacts in an image that result from motion of an object being imaged.
Figure 2B:
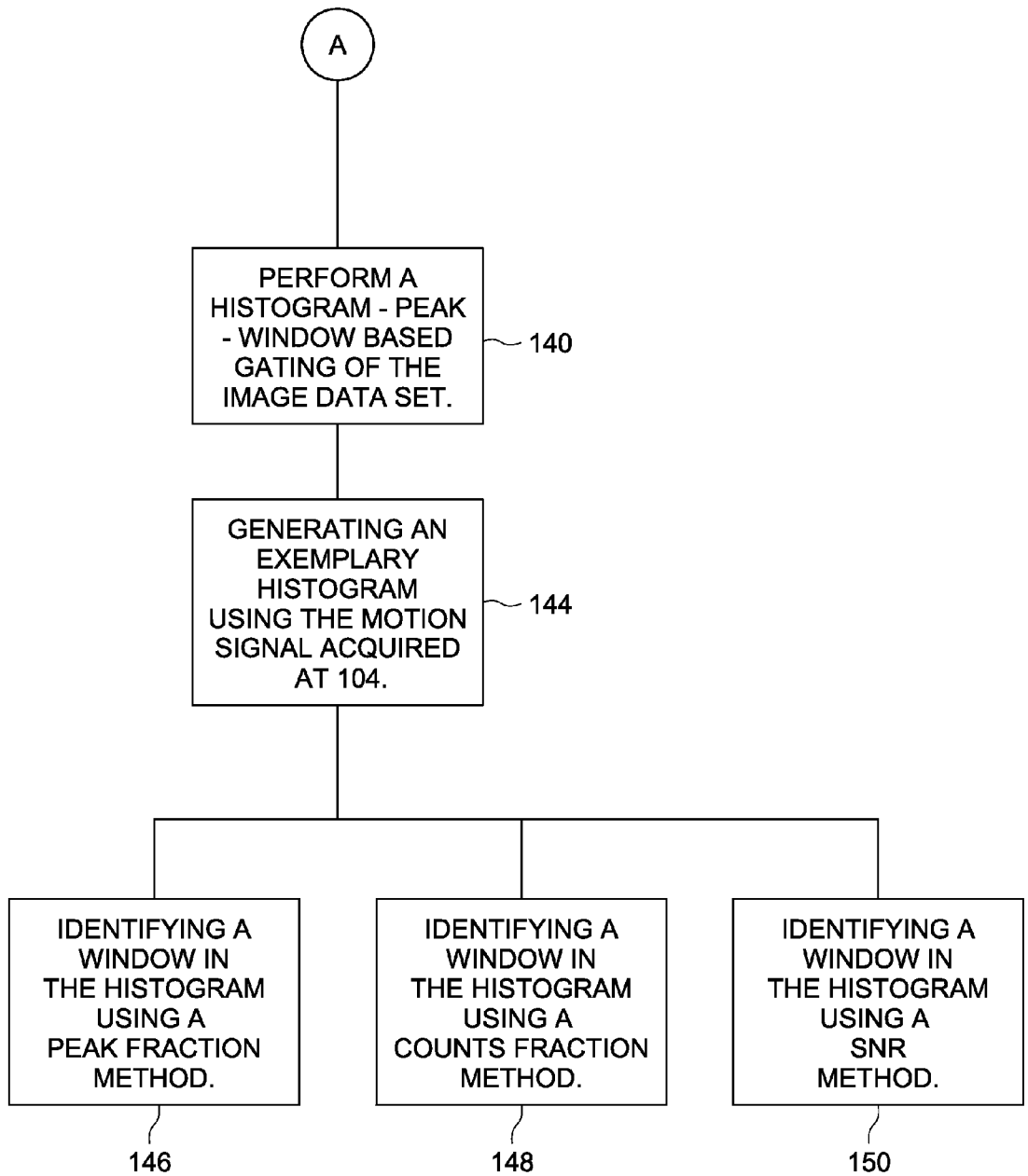

FIG. 2 is a block diagram of an exemplary method 100 for reducing motion related imaging artifacts in an image. The method 100 may be performed by the quiescent period gating module 58 shown in FIG. 1. The method 100 performs quiescent period gating on the image data set 60 to account for the motion of a region of interest of the object 56 based on a motion signal received from a motion sensor 64 shown in FIG. 1. More specifically, the method 100 identifies the motion of the object 56 and re-organizes the image data set 60 to enable a motion-reduced image of the object 56 to be reconstructed. It should be realized that although method 100 is described with respect to the exemplary image data set 60, the method may be applied to an emission data set obtained from a Positron Emission Tomography (PET) imaging system or a Single Photon Emission Computed Tomography (SPECT) imaging system. Moreover, the exemplary image data set may be a transmission data set obtained from a computed tomography (CT) imaging system. The method 100 may be applied to any image data set obtained using any of the imaging modalities discussed herein.

At 102, an image data set, e.g. image data set 60, of a region of interest 66 (shown in FIG. 1) of the object 56 is obtained. In the exemplary embodiment, the image data set 60 is obtained using an imaging system after scanning the object 56. In one embodiment, the image data set 60 is obtained and utilized by the quiescent period gating module 58 in substantially real-time. More specifically, the quiescent period gating module 58 processes the image data set 60 as the data is received from the detector 52. Optionally, the image data set 60 may access stored data, e.g. list mode data, to generate the abridged image data set 62.

Figure 3:
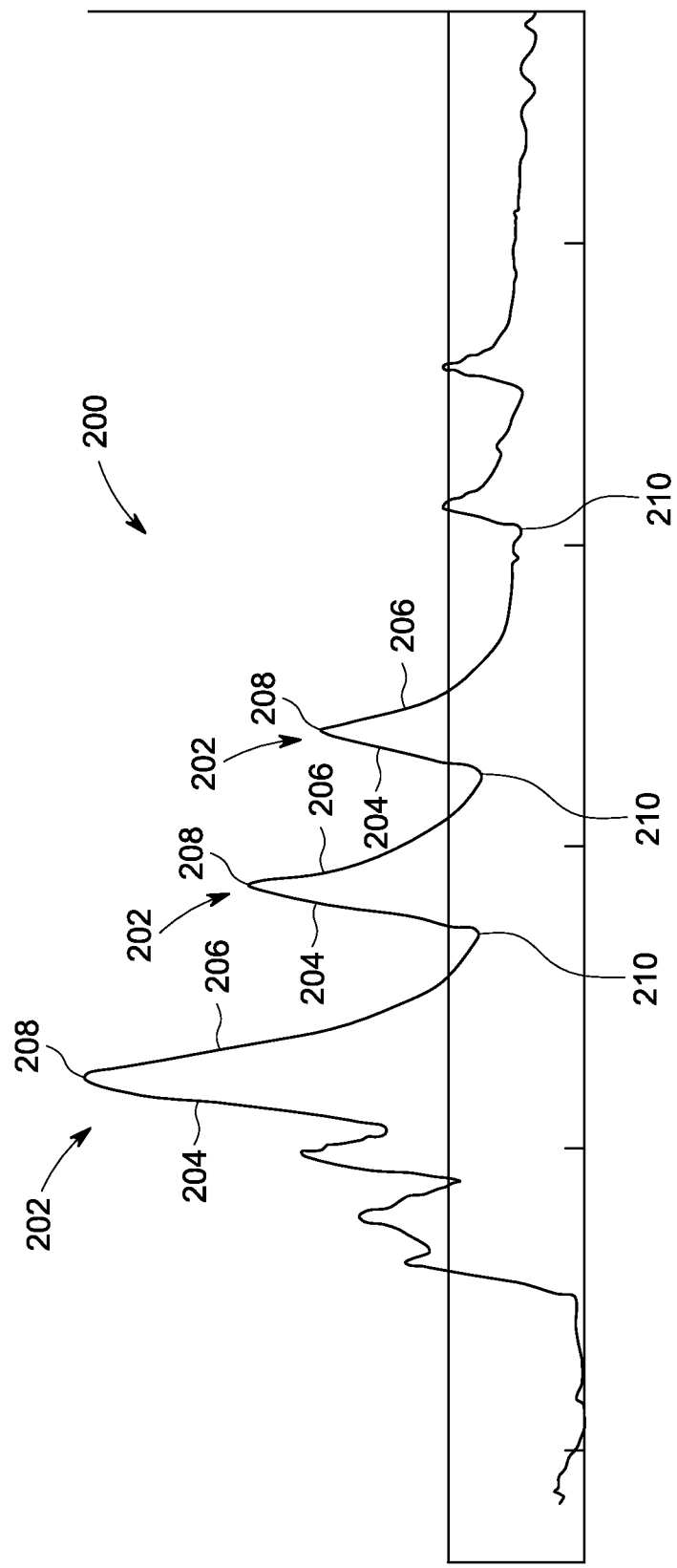
FIG. 3 is a graphical illustration of the exemplary motion signal acquired using the imaging system shown in FIG. 1.

At 104 a signal indicative of motion of the region of interest 66 of the object 56 is obtained. For example, FIG. 3 illustrates an exemplary motion signal 200 that is obtained at 104. The motion signal 200 may be obtained during a PET imaging scan, during a CT imaging scan, or during any other medical imaging system scanning procedure. The motion signal may be either externally measured or measured from the acquired data. As shown in FIG. 3, the Y-axis represents a displacement of the motion signal 200 and the X-axis represents time. In the exemplary embodiment, the motion signal 200 is obtained using the motion sensor 64 shown in FIG. 1. Optionally, the motion signal 200 may be obtained from information saved in a memory device housed within or stored separately from the imaging system 50. In the exemplary embodiment, the motion signal 200 is representative of the motion of object 56. The motion signal 200 includes a plurality of cycles 202 wherein each cycle includes a period 204 that is increasing, a period 206 that is decreasing, a maximum displacement value 208, and a minimum displacement value 210. In the exemplary embodiment, the quiescent period gating module 58 is adapted to obtain or receive the motion signal 200 from the motion sensor 64.

Referring again to FIG. 2, at 106 the quiescent period gating module 58 determines at least one quiescent period of at least a portion of the motion signal 200. The quiescent period gating module 58 utilizes the determined quiescent period to perform quiescent gating as is discussed in more detail below. For example, in one embodiment, the quiescent period gating module 58 utilizes the determined quiescent period to perform a displacement histogram-based gating of the image data set 60. More specifically, at 120, the quiescent period gating module 58 receives the motion signal 200 generated at 104. For example, FIG. 4 is a graphical illustration of the exemplary motion signal 200 and an illustration of the histogram-based gating performed by the quiescent period gating module 58.

Figure 4:
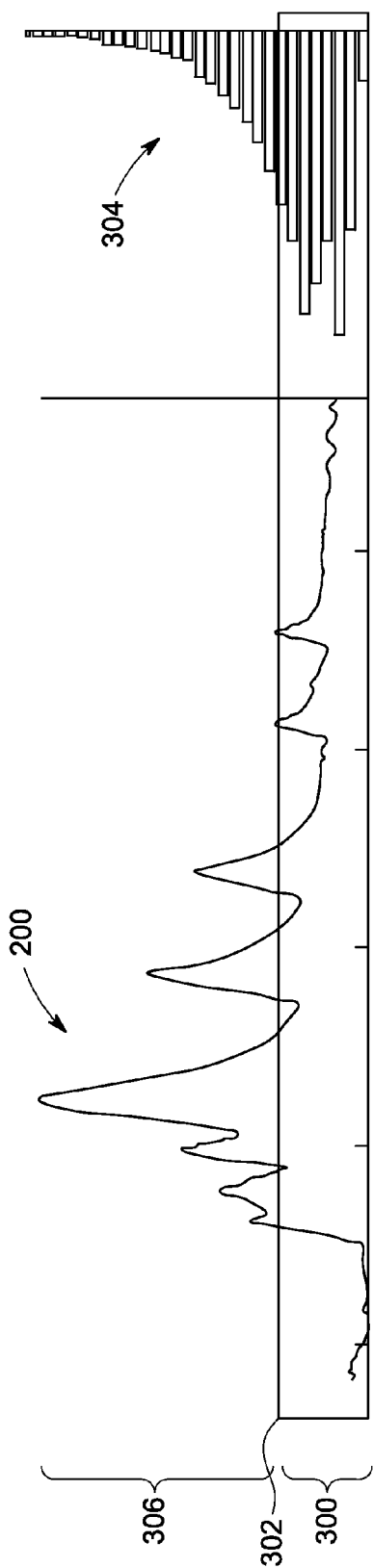
FIG. 4 is a graphical illustration of the exemplary motion signal shown in FIG. 3.

As shown in FIG. 4, the quiescent period gating module 58 is configured to divide the motion signal 200 into intervals based on the displacement of the motion signal 200. More specifically, referring again to FIG. 2, at 124, a histogram 304 of the motion signal 200 is constructed. The threshold 302 can then be set such that the portions 306 of the motion signal 200 contributing to the non-quiescent portion of the data are excluded. The portions 306 are disregarded and the remaining portions 300 of the motion signal 200 are used to generate the image. In other embodiments, the threshold 302 is determined as a certain percentage of the maximum displacement over the whole motion signal 200. At 126, the quiescent period gating module 58 identifies portions of the motion signal 200 that have displacement below a predetermined threshold. For example, referring to FIG. 4, the quiescent period gating module 58 selects image data 300 where the corresponding motion signal 200 is below a threshold 302 regardless of the cycle of the motion signal 200. The selecting step therefore substantially disregards portions 306 of the motion signal 200 that have relatively large displacement from the quiescent period. At 128, the selected image data is used to generate an image of the object 56.

Referring again to FIG. 2, optionally the quiescent period gating module 58 utilizes the determined quiescent period to perform a cycle-based gating 130 of the image data set 60. During operation, the cycle-based gating method 130 is configured to extract image data from the image data set 60 that corresponds to periods where, for each cycle, the motion signal 200 is below or less than a predetermined threshold.

Figure 5:
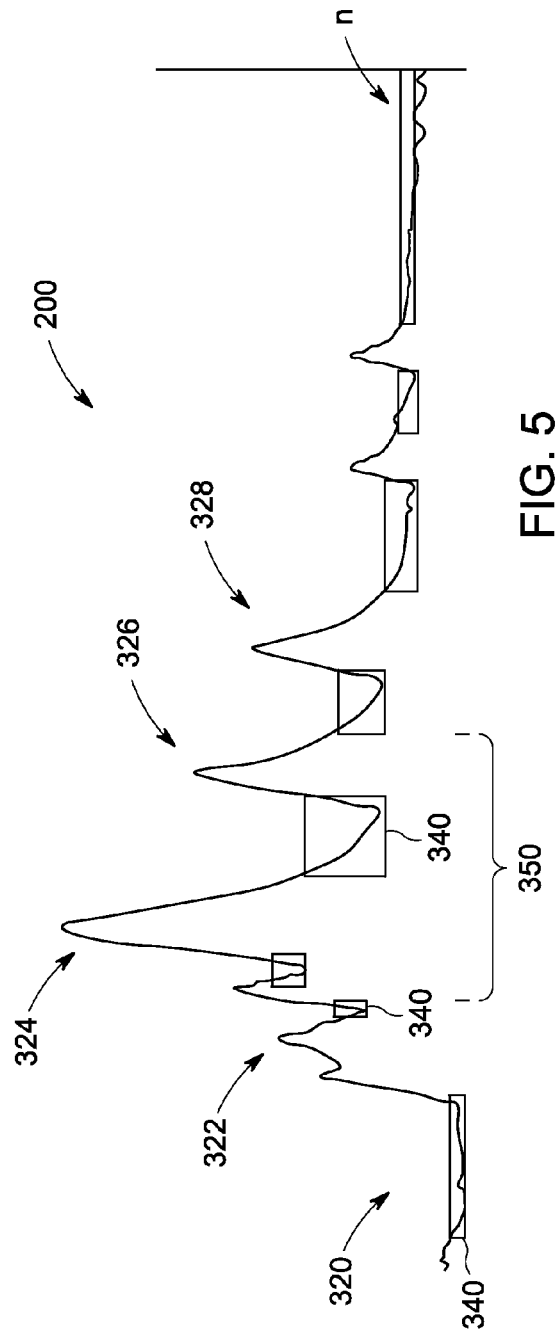
FIG. 5 is a graphical illustration of an exemplary cycle-based gating performed by the quiescent period gating module shown in FIG. 1 in accordance with an embodiment of the present invention.

For example, at 134, the quiescent period gating module 58 identifies individual cycle portions of the motion signal 200. For example, as shown in FIG. 5, the motion signal 200 includes a plurality of cycles 320, 322, 324, 326, 328, 330 . . . n. In the exemplary embodiment, the quiescent period gating module 58 identifies the individual cycles 320 . . . n based on the amplitude of the motion signal 200. For example, the quiescent period gating module 58 may classify the peaks and valleys of the motion signal based on the varying amplitude of the motion signal. After the various cycles of the motion signal 200 are determined, at 136, the quiescent period gating module 58 identifies a quiescent period for each individual cycle 320 . . . n. In one embodiment, the quiescent period gating module 58 utilizes a trigger to determine the portions of each cycle 320 . . . n that are in the quiescent period. For example, a trigger 340 or threshold 340 may be set either by the operator or by the quiescent period gating module 58. Based on the set point of the trigger 340, the quiescent period gating module 58 identifies the portions of the motion signal 200, for each cycle 320 . . . n that are less than the threshold 340, e.g. the portions of the motion signal 200, for each cycle, that are in the quiescent period.

Referring again to FIG. 5, the cycle-based method 130 extracts the portion of the image data 60 where the motion signal 200 is below the threshold 340 for each individual cycle 320 . . . n. In the exemplary embodiment, the threshold 340 is set such that the period where the motion signal 200 is below approximately 20% of the amplitude in each cycle is selected. At 138, the data identified at 136 is used to reconstruct an image of the object 56.

For example, a motion signal having significant amplitude variations and baseline shift may result in images that are not properly correlated or registered. The histogram-base method 120 described above enables images with less motion signal variation to be generated. Moreover, when the motion signal 200 does not have significant amplitude variation and baseline shift, both methods 120 and 130 provide similar image quality. As discussed above, the cycle-based method 130 extracts image data for each cycle that is below or smaller than a predetermined threshold. However, the motion signal 200 may include significant amplitude variations. That is, the peaks, or maximum displacement, for one cycle may be different than the maximum displacement of another cycle in the same motion signal. In this case, the method 130 further includes, identifying two cycles having different amplitudes and then averaging the two amplitudes together. For example, the motion signal 200 includes a cycle 324 that has an amplitude that is greater than the amplitude of a cycle 326. In this case, the amplitude of the cycle 324 and the cycle 326 may be averaged. The threshold 340 is set such that the image data that is below approximately 20% of the averaged amplitude is selected as the quiescent period. The image data corresponding to this quiescent period is then used to reconstruct an image of the object 58.

Figure 6:
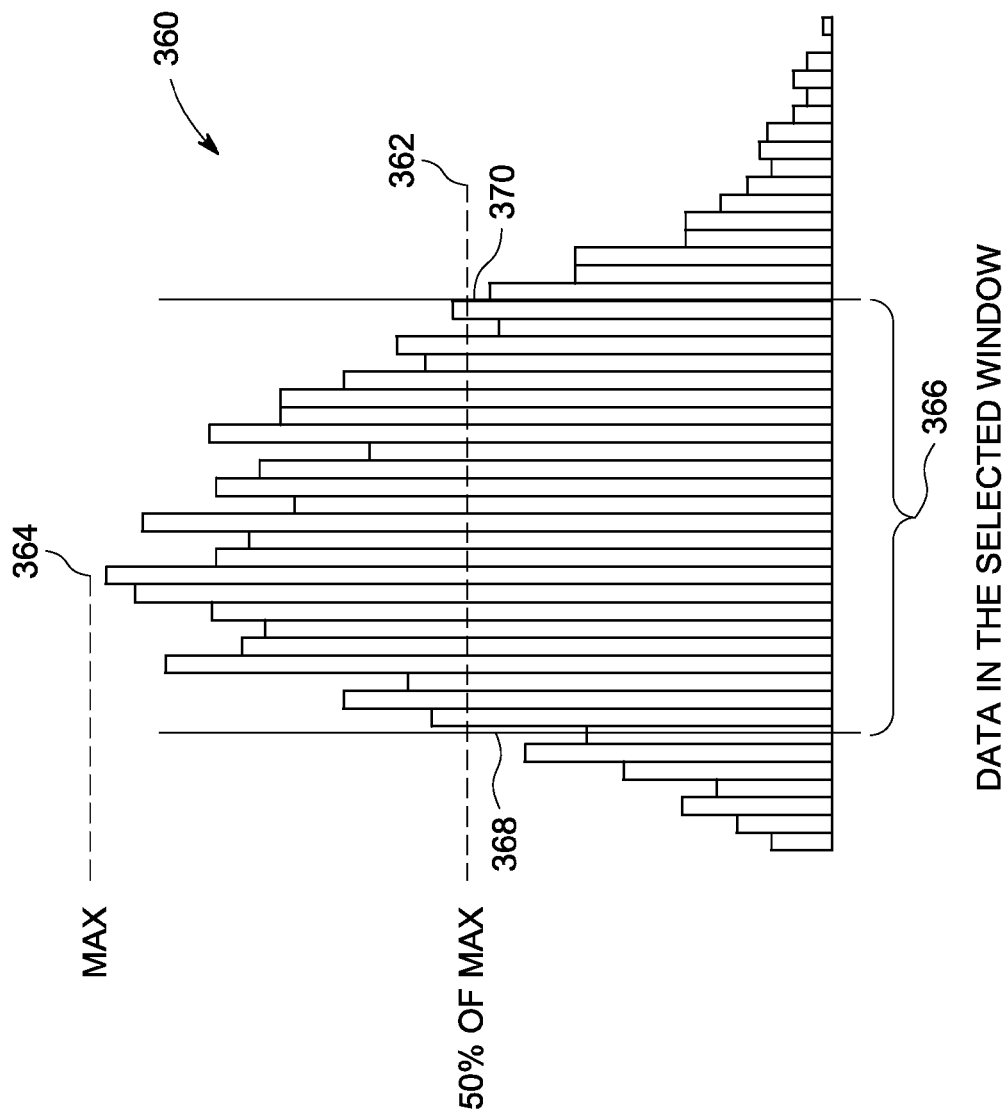
FIG. 6 illustrates an exemplary histogram generated in accordance with an embodiment of the present invention.

Referring again to FIG. 2, in another exemplary embodiment, the quiescent period gating module 58 utilizes the determined quiescent period to perform a histogram-peak-window based gating 140 of the image data set 60. The method 140 includes generating 144 an exemplary histogram using the motion signal 200. For example, FIG. 6 illustrates an exemplary motion signal displacement histogram 360 that is generated in accordance with an embodiment of the present invention. The method 140 further includes identifying a peak window in the histogram 360.

In one embodiment, the peak window is identified using a peak fraction method 146. The peak fraction method 146 includes determining a threshold 362 as a fraction of the maximum value of the histogram 360. In some embodiments, the threshold 362 is approximately 50% of a maximum 364 of the histogram 360. A displacement boundary 366 is then selected. In the exemplary embodiment, the displacement boundary or displacement window 366 is selected as the intersection of the threshold 362 with the displacement histogram 360. More specifically, as shown in FIG. 6, the displacement boundary 366 is defined between a portion 368 and a portion 370 that each extend past the threshold 362 and all the data in between portions 368 and 370. The image data acquired when the motion signal 200 has a displacement within the displacement boundary 366 is then used to reconstruct an image of the object 56. In the exemplary embodiment, the threshold 362 is selected by the operator to either include or exclude image data from the displacement boundary 366.

In another exemplary embodiment, the displacement window 366 is identified at 148 using a counts fraction method. The counts fraction method 140 is similar to the peak fraction method 146 discussed above. However, in the exemplary embodiment, at 148, the threshold 360 is selected such that a predetermined fraction of the total counts is included in the window 366. In the exemplary embodiment, the predetermined quantity of counts is selected by the operator. For example, the operator may select the window 366 such that approximately 45% of the total counts shown in the histogram 360 are within the window 366.

In another exemplary embodiment, the displacement window 366 is identified at 150 using a signal-to-noise ratio (SNR) method. More specifically, the fraction of counts included in the window 366 is related to image noise. Moreover, the displacement range of the window 366 is related to the effect of motion blur. Image noise decreases with a larger fraction of counts and the image is less blurred (more signal) with smaller displacement range. Therefore, the method at 150 includes defining a signal-to-noise ratio (SNR) that enables the highest SNR to be used with the histogram peak window 366.

Figure 7:
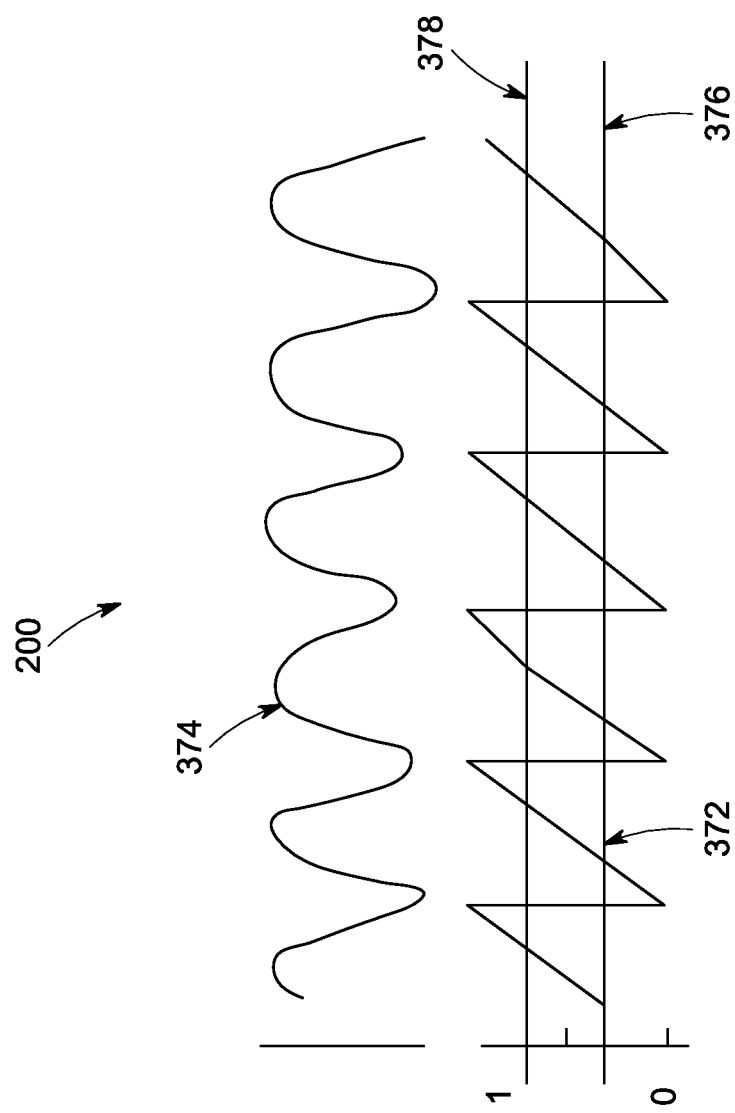
FIG. 7 is a graphical illustration of an exemplary motion signal and cycle-based signal generated using the method described herein in accordance with an embodiment of the present invention.

Referring again to FIG. 2, at 108, the quiescent period gating module 58 is also configured to perform a phase-based gating of the image data set 60. More specifically, at 112, the quiescent period gating module 58 identifies at least one quiescent period of the motion signal 200. As shown in FIG. 7, the quiescent period gating module 58 is configured to determine a phase 372 during the cycle based on the motion signal 200. In one embodiment, a device may generate a trigger at a particular point in the breathing cycle. The phase may be determined using the percent time between two triggers. In another embodiment, the monitoring device 64 computes the phase from the motion signal 200 and makes it available to the quiescent period gating module 58. In another embodiment, the quiescent period gating module 58 computes the phase on the motion signal 200. For example, to determine inspiration (I), expiration (E), end-of-inspiration (EI) and end-of-expiration (EE) phases, the following procedure may be implemented:

$$d = (\tilde{A}(t) - \tilde{A}(t-\Delta)) \quad \text{(Eqn. 1)}$$

if $d > T_1(t)$, then s=I, else if $d < T_2(t)$ then s=E, else if the previous phase s was I, then s=EI, else s=EE.

where s is the phase, $T_1$ and $T_2$ are (potentially time-dependent) thresholds and $(\tilde{A}(t))$ denotes the (optionally processed) motion signal 200 at a given time; and $\Delta$ denotes a time constant that is pre-selected based on the expected cycle duration; for example $\Delta \approx 200$ milliseconds. In one embodiment, $\Delta$ may be smaller than an expected period of the phase of the motion signal 200. $\Delta$ may be significantly smaller than the phase period, but not so small that $\Delta$ would be sensitive to noise. By way of example only, $\Delta$ may be less than one tenth of the phase period of the motion signal 200. In one embodiment, the motion signal is processed using a denoising filter. For example, $(\tilde{A}(t))$ would be computed by a running average of the original signal $(A(t))$. It should be clear that other embodiments exist that use other known methods to determine phase for a quasi-periodic signal.

In the exemplary embodiment, the motion signal 200 is used for phase gating to determine if the patient is in the end-of-expiration phase 374. In the exemplary embodiment, the quiescent period gating module 58 utilizes a threshold 376 on the phase to determine when the quiescent period starts and a threshold 378 to determine when it ends. The thresholds 376 and 378 may be set either by the operator or by the quiescent period gating module 58. In one embodiment, a histogram is computed of the values of d determined by Eqn. 1 in terms of the phase. The thresholds 376 and 378 may then be set in similar ways as discussed above for the displacement histograms. At 114, the image data obtained at 112 is used to generate an image of the object.

In some embodiments, the above described methods 108, 120, and/or 130 may be combined to further improve the quality of quiescent period gating. For example, the cycle-based method 130 may be first applied to the image data set 60 to extract the data corresponding to the quiescent period. The histogram-peak-window-based method 130 may then be applied to extract data to reject the outliers.

Figure 8:
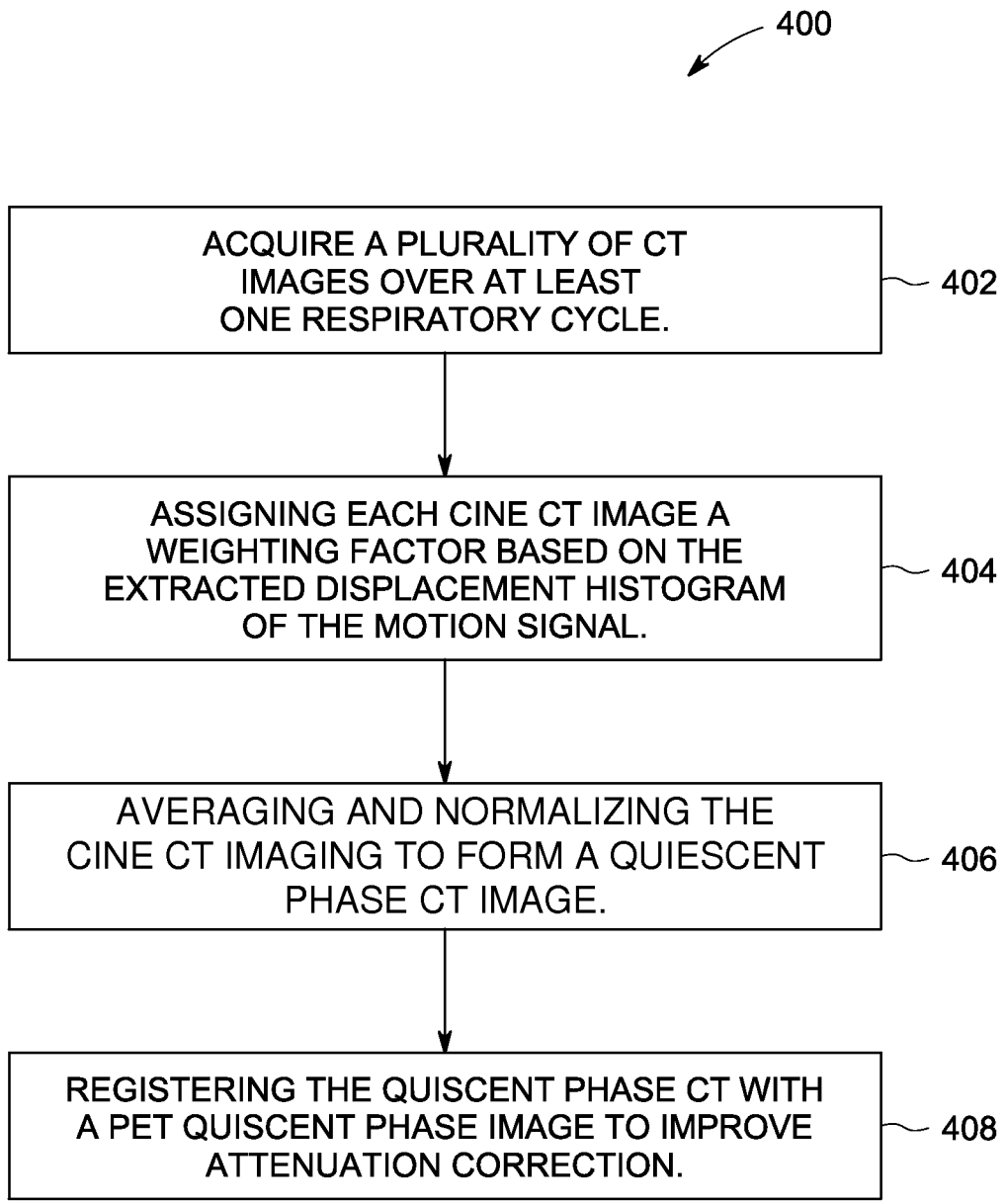
FIG. 8 is a flowchart illustrating another exemplary method in accordance with various embodiments for reducing motion artifacts in an image that result from motion of an object being imaged.
Figure 9:
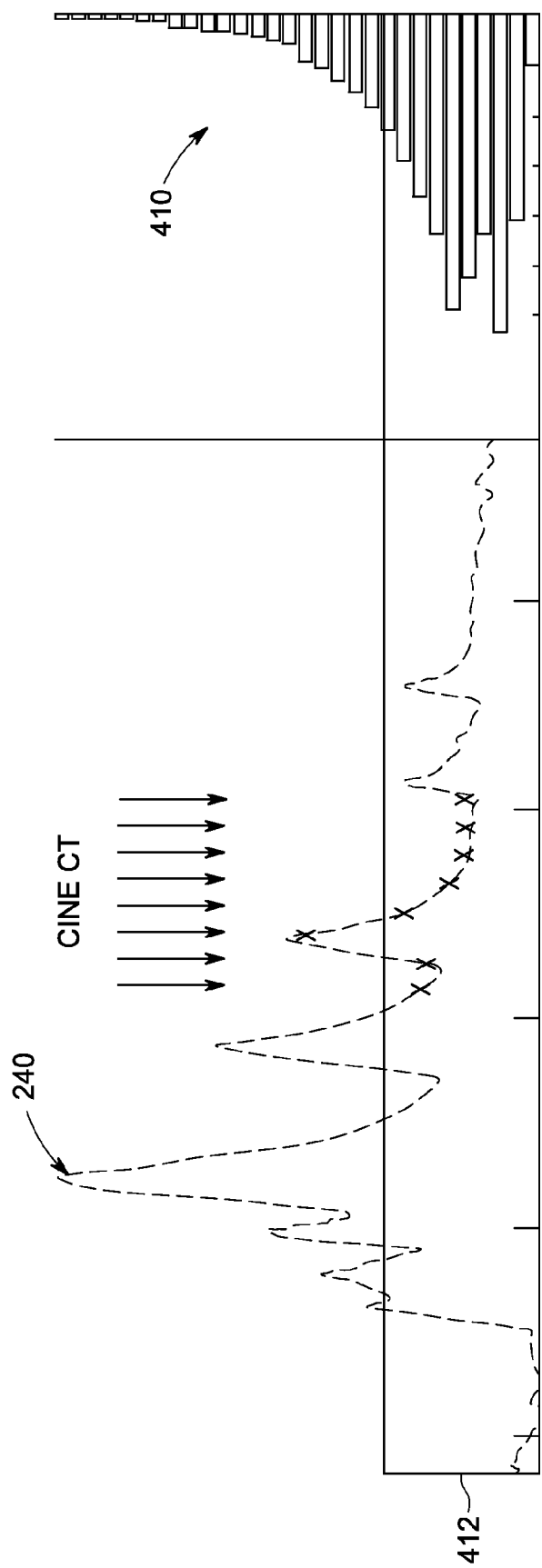
FIG. 9 illustrates an exemplary histogram generated in accordance with an embodiment of the present invention.

FIG. 8 is a flowchart illustrating another exemplary method 400 for reducing motion related artifacts in an image. In the exemplary embodiment, the method 400 is implemented to perform phase-match attenuation correction using quiescent period computed tomography (CT) images. At 402, a plurality of CT images are acquired over at least one respiratory cycle. The method 400 further includes assigning at 404 each cine CT image a weighting factor based on the extracted displacement histogram of the motion signal 200 acquired during the PET scan. At 406, the weighted cine CT images are averaged and normalized to form a quiescent period CT image. For example, FIG. 9 is a graphical illustration of an exemplary CT motion signal 240 and an extracted displacement histogram 410 that is generated based on the PET motion signal 200 occurring at time points that were selected for a quiescent period during PET. For each CT image, the value of the CT motion signal 240 during the time period in which the CT image was acquired is found. These values are used to find the "frequency" in the histogram 410. The weighting factor can then be chosen as a function of this "frequency". For example, the weighting factor can be set to be proportional to the frequency, with the proportionality factor determined by making sure that the sum of the weighting factors for all CT images contributing to the same location in the object 56 is one. Therefore, in the exemplary embodiment, the cine CT images are weighted based on the motion signal 240 acquired during a CT scan and the parts of the motion signal 200 used to construct the PET image to yield an improved PET-CT match. In the exemplary embodiment, large variations in the amplitude and period occur in motion signals acquired during a PET and CT scan. Optionally, the method 400 also includes registering at 408 the quiescent period CT image with a PET quiescent period image to improve attenuation correction.

Figure 10:
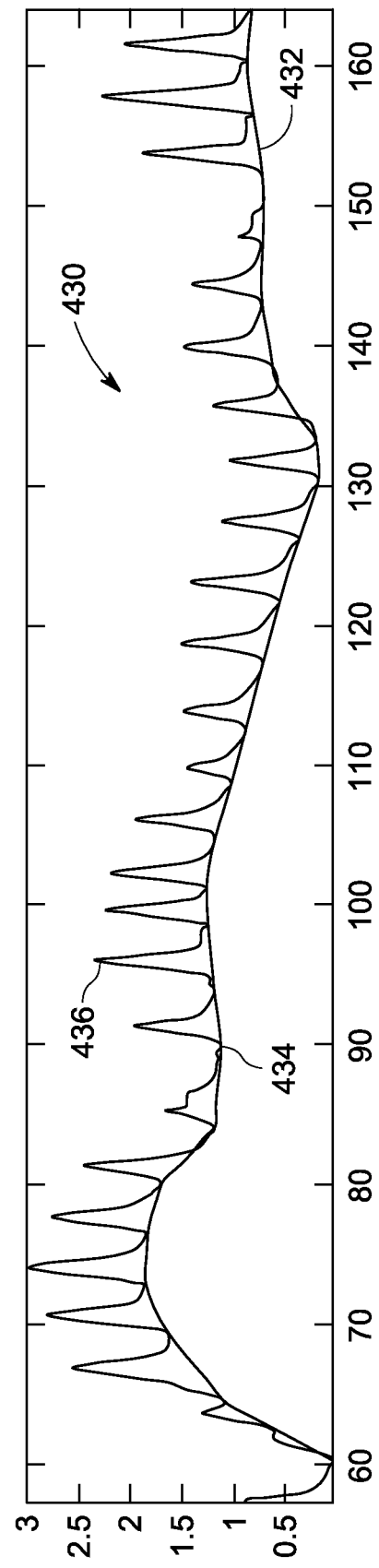
FIG. 10 is a graphical illustration of an exemplary motion signal having a baseline shift.
Figure 11:
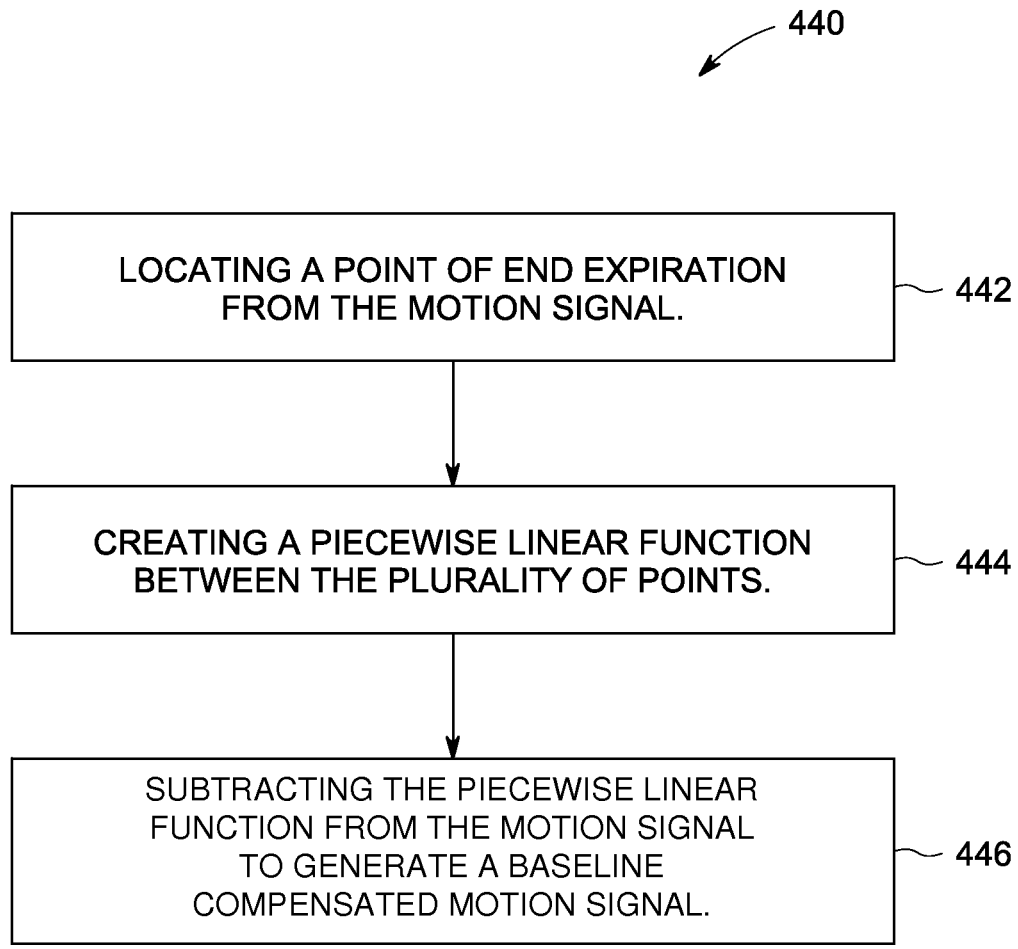
FIG. 11 is a flowchart illustrating an exemplary method for applying a baseline correction algorithm to the motion signal shown in FIG. 10 in accordance with an embodiment of the present invention.

Each of the methods described herein may also include performing a baseline shift correction on the motion signal 200 and/or the motion signal 412. For example, FIG. 10 is a graphical illustration of an exemplary motion signal 430 having a baseline shift. As shown in FIG. 10, a piece-wise linear function 432 is shown to illustrate the baseline shift between the end expiration points 434 of each cycle 436. Moreover, as shown in FIG. 10, a displacement of the patient's motion signal at the end of respiration may vary over time. This variance is often referred to as a baseline shift, which may be caused by several contributing factors, such as the patient relaxing during the scan or the deflection of the scanning bed. To optimize the correlation between the patient position and the motion signal displacement, FIG. 11 illustrates an exemplary method 440 for applying a baseline correction algorithm to the motion signal 430 and to compensate for the baseline shift. In the exemplary embodiment, the compensation method 440 is based on the gating method implemented and the nature of the motion signal 430. During operation, the compensation method 440 may be used in conjunction with any of the quiescent period gating methods described above to compensate for motion signals having significant baseline changes.

Figure 12:
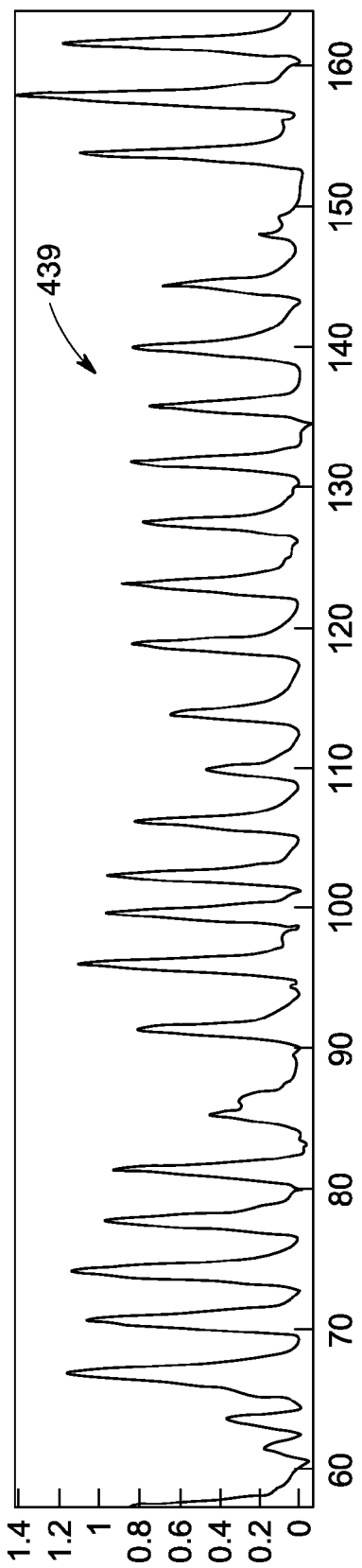
FIG. 12 is a graphical illustration of an exemplary motion signal corrected using the method shown in FIG. 11.

In one embodiment, method 440 includes at 442 locating a point 434 of end expiration for a plurality of cycles 436 in the motion signal 430. The method 440 further includes creating at 444 a piece-wise linear function 438 between the points 434. At 446, the piece-wise linear function 438 is subtracted from the motion signal 430 to generate a baseline compensated motion signal 439 as shown in FIG. 12. In another embodiment, the method 440 includes creating a piece-wise constant function, which is defined as the end expiration displacement over each respiratory cycle. The piece-wise constant function is then subtracted from the motion signal 430 shown in FIG. 10 to generate the baseline shift corrected motion signal shown in FIG. 12. In the exemplary embodiment, the piece-wise functions may be defined over different intervals or at different bed positions. In other embodiments, other interpolating functions may be used, such as B-splines. Moreover, the interpolating functions may also combined for a baseline compensation technique most appropriate for the gating method being used.

In another embodiment, the gating methods described herein may be applied differently to the inspiration phase and/or the expiration phase of a motion signal. For example, internal organs may move differently based on whether the patient is in inspiration or expiration. Accordingly, the different quiescent period gating methods described herein may be modified such that the image data is extracted only during expiration, e.g. the quiescent period, and the remaining data discarded. The extracted data is then used to reconstruct an image of the object. The quiescent period gating methods considering only expiration data further improve the tracer uptake quantification with some sacrifice on the counts. As an example embodiment based on the displacement histogram technique is described below, but it should be clear that this technique applies to other embodiments as well.

During each of the methods described herein, the quiescent period gating module 58 is configured to prohibit data inclusion into the quiescent period based on predetermined criteria. Such criteria may include comparing the standard uptake value maximum ($SUV_{max}$) for a feature for a given histogram threshold to the same measure using data with a random motion component from the PET listmode data but statistically matched (in total counts) to the quiescent period data. Results for several thresholds are found and summarized for the user to enable clinical decision-making. Additionally, the selected quiescent period image can be compared with the image formed using the remaining listmode data. With sufficient statistics, a SUVmax difference between images with two different settings may provide useful information on the threshold selection.

Figure 13:
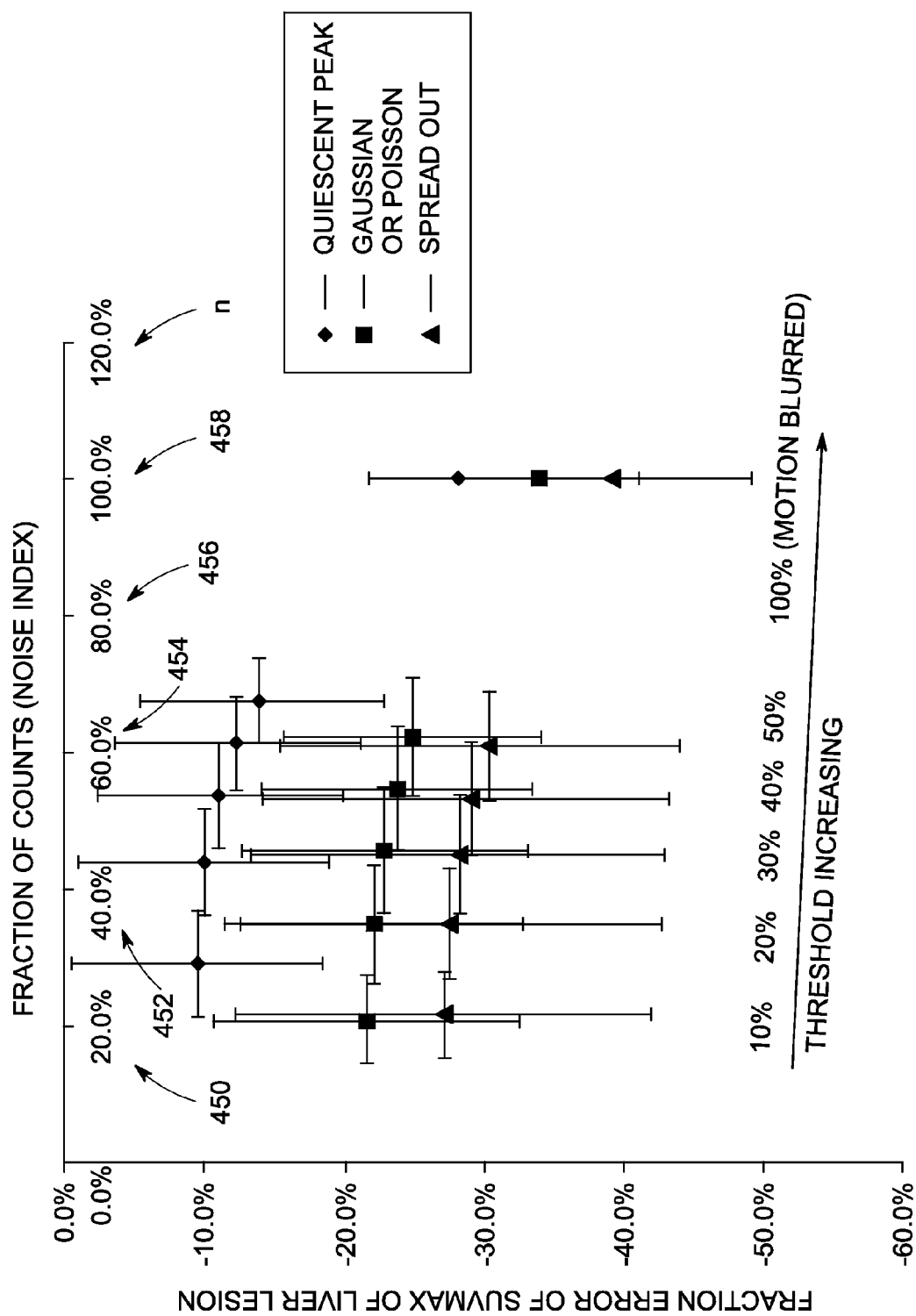
FIG. 13 is an exemplary illustration of computer simulations of an exemplary phantom and actual patient respiratory traces in accordance with an embodiment of the present invention.

In the exemplary embodiment, the methods described herein may also include optimizing parameters of the quiescent period gating methods. For example, during operation, the quiescent period gated PET images may become more blurred but less noisy with increasing quiescent period thresholds. Therefore, an optimal quiescent period threshold is selected based on the blur-to-noise (SNR) tradeoff for a particular imaging task. For example, based on a computer simulations of an exemplary phantom and actual patient respiratory traces, the relationship of tumor quantification (for instance in terms of $SUV_{max}$) error and fraction of counts used (surrogate of noise index) can be established for different tumor size, tumor location, tumor contrast, patient breathing pattern, motion amplitude, and quiescent period threshold, as the example shown in FIG. 13. Therefore, for each patient study, a motion signal histogram is presented to the operator. The operator may then identify different motion signal categories. Moreover, the operator may select several threshold levels 450, 452, 454, 456, 458 . . . n that correspond with the $SUV_{max}$ and noise index to let the operator determine the desired quiescent period threshold. As shown in FIG. 13, the threshold levels 450-n may be 20%, 40%, 60%, 80%, etc.

A technical effect of the various embodiments is to provide a method and apparatus for performing quiescent period-based gating to reduce motion related imaging artifacts caused by respiration or other quasi-periodic movements in either transmission or emission data. Described herein are methods and apparatuses for performing quiescent period gating. In one embodiment, quiescent data is selected from PET list-mode data, regardless of motion (i.e. formation of a short STATIC PET scan). Results for several thresholds are found and summarized for the user to select an appropriate setting based on the medical condition being evaluated. The methods and systems described herein also improve PET-CT lesion quantification and volume determination while conserving image quality. These methods also are intended to be clinically relevant with respect to processing and time-to-results. Moreover, the methods reduce the impact of patient respiratory motion on diagnostic usefulness of imaging results and is a major benefit to the PET-CT system.

Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

Figure 14:
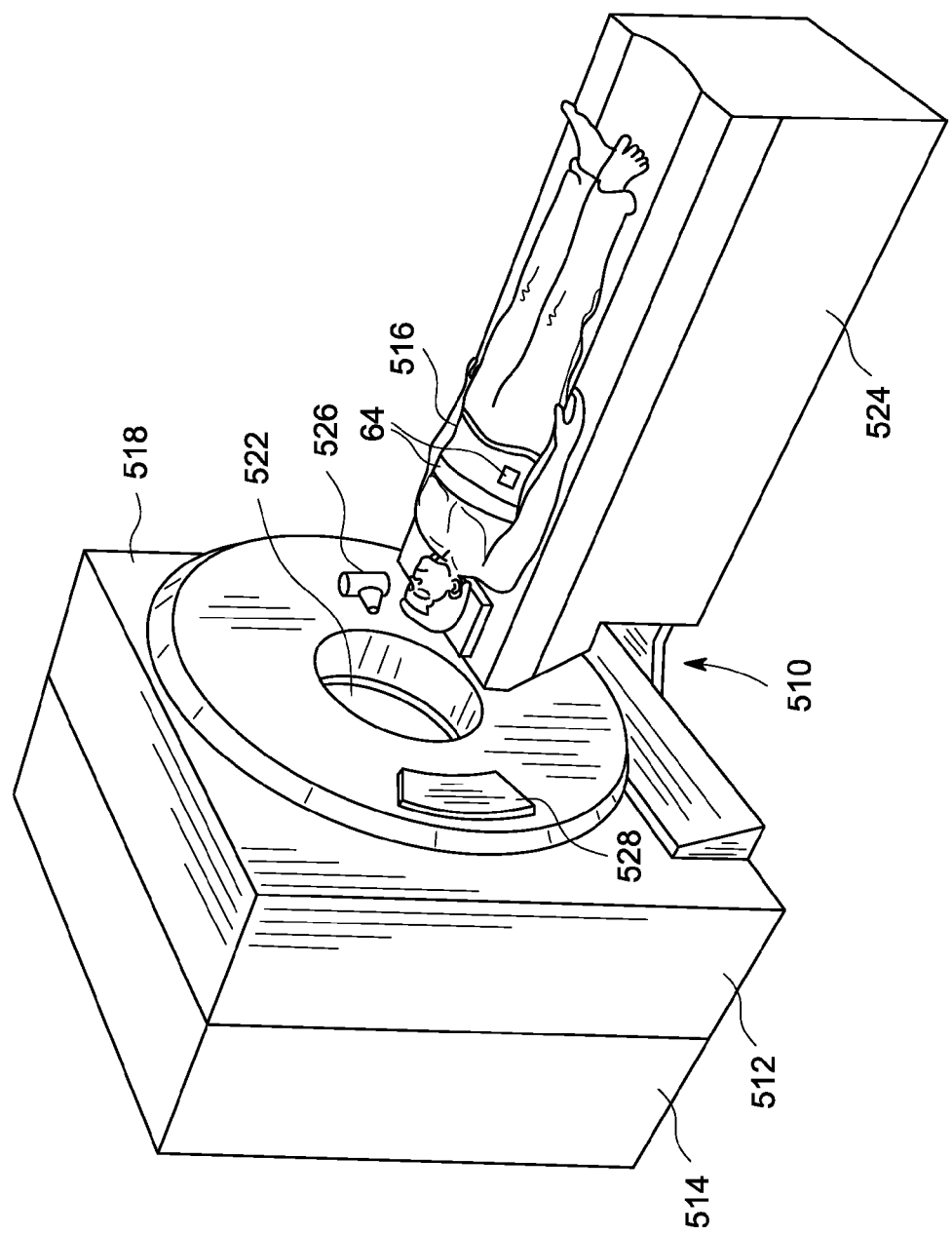
FIG. 14 is a pictorial view of an exemplary multi-modality imaging system formed in accordance with an embodiment of the present invention.
Figure 15:
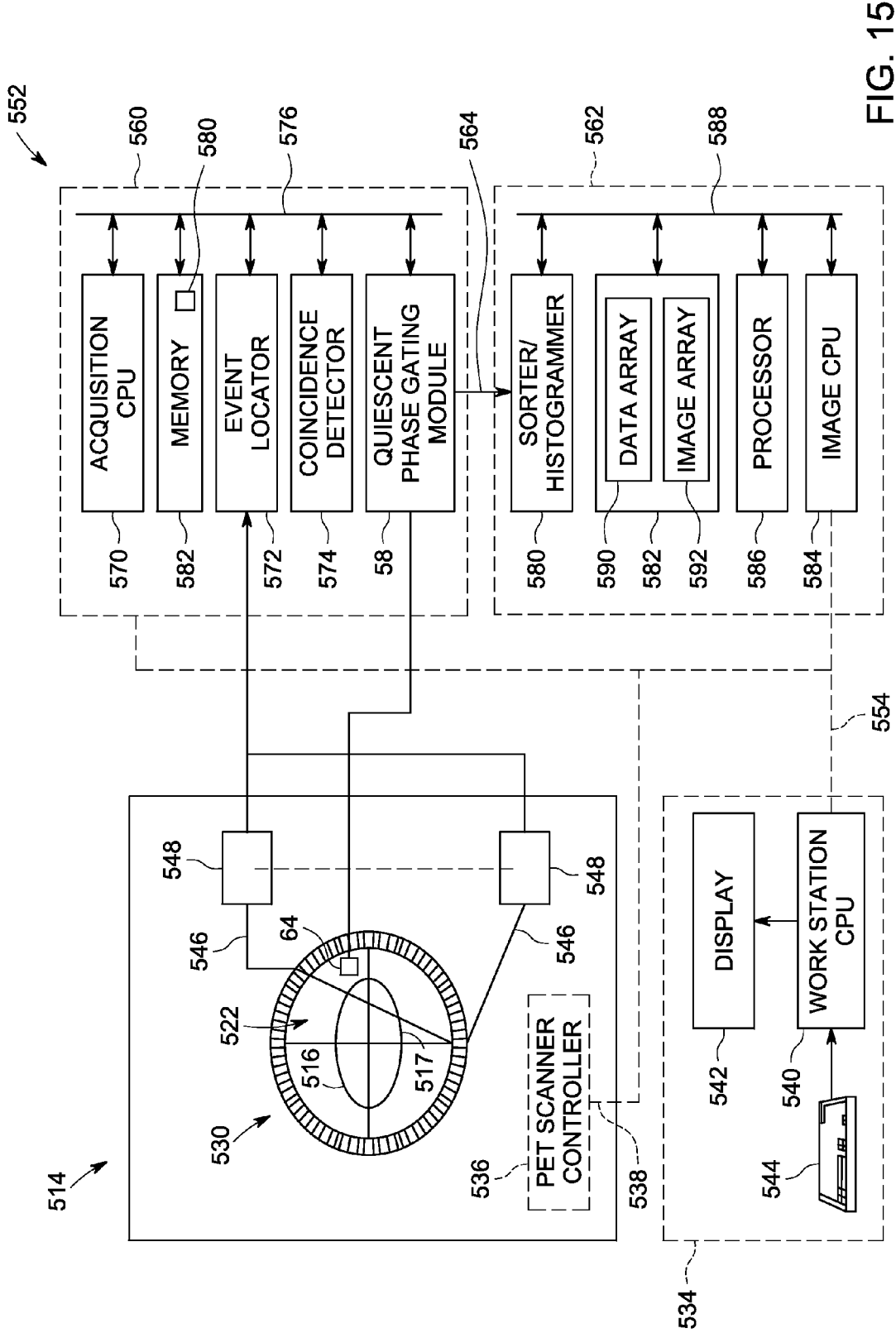
FIG. 15 is a block schematic diagram of the system illustrated in FIG. 14 formed in accordance with an embodiment of the present invention.

The quiescent period gating module 58 may be utilized with an exemplary medical imaging system, such as the imaging system 510 shown in FIGS. 14 and 15. In the exemplary embodiment, the imaging system 510 is a multi-modality imaging system that includes different types of medical imaging systems, such as a Positron Emission Tomography (PET), a Single Photon Emission Computed Tomography (SPECT), a Computed Tomography (CT), an ultrasound system, Magnetic Resonance Imaging (MRI) or any other system capable or generating images. The quiescent period gating module 58 described herein is not limited to multi-modality medical imaging systems, but may be used on a single modality medical imaging system such as a stand-alone PET imaging system or a stand-alone SPECT imaging system, for example. Moreover, the quiescent period gating module 58 is not limited to medical imaging systems for imaging human subjects, but may include veterinary or non-medical systems for imaging non-human objects etc.

Referring to FIG. 14, the multi-modality imaging system 510 includes a first modality unit 512 and a second modality unit 514. The two modality units enable the multi-modality imaging system 510 to scan an object or patient, such as object 516 in a first modality using the first modality unit 512 and to scan the object 516 in a second modality using the second modality unit 514. The multi-modality imaging system 510 allows for multiple scans in different modalities to facilitate an increased diagnostic capability over single modality systems. In one embodiment, first modality unit 512 is a Computed Tomography (CT) imaging system and the second modality 514 is a Positron Emission Tomography (PET) imaging system. The CT/PET system 510 is shown as including a gantry 518. During operation, the object 516 is positioned within a central opening 522, defined through the imaging system 510, using, for example, a motorized table 524. The gantry 518 includes an x-ray source 526 that projects a beam of x-rays toward a detector array 528 on the opposite side of the gantry 518.

The imaging system 510 optionally also includes one or more motion sensors 64 that is adapted to detect and transmit information that is indicative of the motion of the object 516. In one embodiment, the motion sensor 64 may be a belt-type motion sensor that is adapted to extend at least partially around the object 516. Optionally, the motion sensor 64 may be a motion sensor that is adapted to be secured to a predetermined position on the object 516. It should be realized that although two different motion sensors or detectors are illustrated, that the imaging system may include other types of motions sensors to generate motion related information.

FIG. 15 is a block schematic diagram of an exemplary PET imaging system 514 in accordance with an embodiment of the present invention. The PET imaging system 514 includes a detector ring assembly 530 including a plurality of detector scintillators. The detector ring assembly 530 includes the central opening 522, in which an object or patient, such as object 516 may be positioned, using, for example, a motorized table 524 (not shown in FIG. 14). The scanning operation is controlled from an operator workstation 534 through a PET scanner controller 536. A communication link 538 may be hardwired between the PET scanner controller 536 and the workstation 534. Optionally, the communication link 538 may be a wireless communication link that enables information to be transmitted to or from the workstation to the PET scanner controller 536 wirelessly. In the exemplary embodiment, the workstation 534 controls real-time operation of the PET imaging system 514. The workstation 534 is also programmed to perform medical image diagnostic acquisition and reconstruction processes described herein. The operator workstation 534 includes a central processing unit (CPU) or computer 540, a display 542 and an input device 544. As used herein, the term "computer" may include any processor-based or microprocessor-based system configured to execute the methods described herein.

The methods described herein may be implemented as a set of instructions that include various commands that instruct the computer or processor 540 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

During operation of the exemplary detector 530, when a photon collides with a scintillator on the detector ring assembly 530, the absorption of the photon within the detector produces scintillation photons within the scintillator. The scintillator produces an analog signal that is transmitted on a communication link 546 when a scintillation event occurs. A set of acquisition circuits 548 is provided to receive these analog signals. The acquisition circuits 548 produce digital signals indicating the 3-dimensional (3D) location and total energy of each event. The acquisition circuits 548 also produce an event detection pulse, which indicates the time or moment the scintillation event occurred.

The digital signals are transmitted through a communication link, for example, a cable, to a data acquisition controller 552 that communicates with the workstation 534 and PET scanner controller 536 via a communication link 554. In one embodiment, the data acquisition controller 552 includes a data acquisition processor 560 and an image reconstruction processor 562 that are interconnected via a communication link 564. During operation, the acquisition circuits 548 transmit the digital signals to the data acquisition processor 560. The data acquisition processor 560 then performs various image enhancing techniques on the digital signals and transmits the enhanced or corrected digital signals to the image reconstruction processor 562 as discussed in more detail below.

In the exemplary embodiment, the data acquisition processor 560 includes at least an acquisition CPU or computer 570. The data acquisition processor 560 also includes an event locator circuit 572 and a coincidence detector 574. The acquisition CPU 570 controls communications on a back-plane bus 576 and on the communication link 564. During operation, the data acquisition processor 560 periodically samples the digital signals produced by the acquisition circuits 548. The digital signals produced by the acquisition circuits 548 are transmitted to the event locator circuit 572. The event locator circuit 572 processes the information to identify each valid event and provide a set of digital numbers or values indicative of the identified event. For example, this information indicates when the event took place and the position of the scintillator that detected the event. The events are also counted to form a record of the single channel events recorded by each detector element. An event data packet is communicated to the coincidence detector 574 through the back-plane bus 576.

The coincidence detector 574 receives the event data packets from the event locator circuit 572 and determines if any two of the detected events are in coincidence. Coincident event pairs are located and recorded as a coincidence data packets by the coincidence detector 574 and are communicated through the back-plane bus 576 to a quiescent period gating module 58. The output from the coincidence detector 574 is referred to herein as an emission data set 60 or raw image data. In one embodiment, the emission data set 60 may be stored in a memory device that is located in the data acquisition processor 560. Optionally, the emission data set 60 may be stored in the workstation 534. As shown in FIG. 15, in the exemplary embodiment the output from the motion sensor 64 is also transmitted to the quiescent period gating module 58. The operation of the quiescent period gating module 58 is discussed in more above.

The motion corrected image data set, e.g. the image data subset 62, is then transmitted from the quiescent period gating module 58 to a sorter/histogrammer 80 to generate a data structure known as a histogram. Optionally, the quiescent period gating module 58 may generate the histograms described herein. The image reconstruction processor 562 also includes a memory module 582, an image CPU 584, an array processor 586, and a communication bus 588. During operation, the sorter/histogrammer 580 performs the motion related histogramming described above to generate the events listed in the image data subset 62 into 3D data. This 3D data, or sinograms, is organized in one exemplary embodiment as a data array 590. The data array 590 is stored in the memory module 582. The communication bus 588 is linked to the communication link 576 through the image CPU 584. The image CPU 584 controls communication through communication bus 588. The array processor 586 is also connected to the communication bus 588. The array processor 586 receives the data array 590 as an input and reconstructs images in the form of image arrays 592. Resulting image arrays 592 are then stored in the memory module 582. The images stored in the image array 592 are communicated by the image CPU 584 to the operator workstation 534.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for reducing motion related imaging artifacts, said method comprising:
    obtaining a first image data set of a region of interest in an object;
    obtaining a computed tomography (CT) image data set;
    obtaining, using the first image data set, a motion signal indicative of motion of the region of interest;
    extracting a displacement histogram of the motion signal;
    assigning a weighting factor, based upon the displacement histogram, to a plurality of CT images of the CT image data set to provide weighted CT images; and
    averaging and normalizing the weighted CT images to form a quiescent CT image.

2. A method in accordance with claim 1 wherein obtaining the first image data set further comprises obtaining at least one of a Positron Emission Tomography (PET) emission data set and a Single Photon Emission Computed Tomography (SPECT) emission data set.

3. A method in accordance with claim 1 further comprising identifying a window in the displacement histogram using a peak fraction of the first image data set.

4. A method in accordance with claim 1 further comprising identifying a window in the displacement histogram using a counts fraction of the first image data set.

5. A method in accordance with claim 1 further comprising identifying a window in the displacement histogram using a signal-to-noise ratio of the first image data set.

6. A method in accordance with claim 1 further comprising:
    matching the quiescent CT image with a positron emission tomography (PET) image to improve attenuation correction and PET localization.

7. A method in accordance with claim 1 further comprising applying a baseline correction to the motion signal to compensate for baseline shift.

8. A method in accordance with claim 1, further comprising using a function based on an end of expiration to generate a baseline compensated motion signal from the motion signal.

9. A method in accordance with claim 1, further comprising disregarding inspiration phase data.

10. A multi-modality imaging system comprising a first modality unit, a second modality unit, and a quiescent period gating module operationally coupled to the first and second modality units, wherein the quiescent period gating module is programmed to:
    obtain, based on a first image data set obtained using the first modality unit, a motion signal indicative of motion of a region of interest;
    obtain a computed tomography (CT) image data set using the second modality unit;
    extract a displacement histogram of the motion signal;
    assign a weighting factor, based upon the displacement histogram, to a plurality of images of the CT image data set to provide weighted CT images; and
    average and normalize the weighted CT images to form a quiescent CT image.

11. A multi-modality imaging system in accordance with claim 10, wherein the first modality unit comprises at least one of a Positron Emission Tomography (PET) system and a Single Photon Emission Computed Tomography (SPECT) imaging system.

12. A multi-modality imaging system in accordance with claim 10, wherein the quiescent period gating module is further programmed to identify a window in the displacement histogram using at least one of a peak fraction method, a counts fraction method, and a signal-to-noise ratio method.

13. A multi-modality imaging system in accordance with claim 10, wherein the quiescent period gating module is further programmed to apply a baseline correction to the motion signal to compensate for baseline shift.

14. A multi-modality imaging system in accordance with claim 10, wherein the quiescent period gating module is further programmed to use a function based on an end of expiration to generate a baseline compensated motion signal from the motion signal.

15. A multi-modality imaging system in accordance with claim 10, wherein the quiescent period gating module is further programmed to disregard inspiration phase data.

16. A tangible and non-transitory computer readable medium encoded with a program to instruct a computer to:
    obtain a first image data set of a region of interest in an object from a PET imaging system;
    obtain a computed tomography (CT) image data set;
    obtain a motion signal indicative of motion of the region of interest using the first image data set;
    extract a displacement histogram of the motion signal;
    assign a weighting factor, based upon the displacement histogram, to a plurality of CT images of the CT image data set to provide weighted CT images;
    average and normalize the weighted CT images to form a quiescent CT image.

17. A computer readable medium in accordance with claim 16 wherein the program is programmed to further instruct the computer to:
    identify a window in the displacement histogram using at least one of a peak fraction method, a counts fraction method, and a signal-to-noise ratio method; and
    reconstruct an image of the object of interest using image data identified within the window.

18. A tangible and non-transitory computer readable medium in accordance with claim 16 wherein the program is programmed to further instruct the computer to use a function based on an end of expiration to generate a baseline compensated motion signal from the motion signal.

19. A tangible and non-transitory computer readable medium in accordance with claim 16 wherein the program is programmed to further instruct the computer to disregard inspiration phase data.

* * * * *